US00PP12280P2

(12) United States Plant Patent
Houbraken

(10) Patent No.: US PP12,280 P2
(45) Date of Patent: Dec. 18, 2001

(54) *BIDENS FERULIFOLIUM* PLANT NAMED 'BIDTIS-1'

(75) Inventor: Anna M. W. P. Houbraken, Enkhuizen (NL)

(73) Assignee: Syngenta Seeds B.V., Enkhuiken (NL)

( * ) Notice: Subject to any disclaimer, the term of this patent is extended or adjusted under 35 U.S.C. 154(b) by 0 days.

(21) Appl. No.: 09/500,688

(22) Filed: Feb. 9, 2000

(51) Int. Cl.[7] ..... A01H 5/00
(52) U.S. Cl. ..... Plt./263
(58) Field of Search ..... Plt./263

(56) References Cited

U.S. PATENT DOCUMENTS

P.P. 11,261 * 3/2000 Theobald ..... Plt./263

* cited by examiner

*Primary Examiner*—Bruce R. Campell
*Assistant Examiner*—Wendy C Baker
(74) *Attorney, Agent, or Firm*—Bruce Vrana

(57) ABSTRACT

A new Bidens plant particularly distinguished by its upright character, compact plant habit, reduced seed set and golden yellow flowers. Flowering time is from April till November, depending on the temperature. Better resistance to Botrytis and Powdery mildew than *Bidens ferulifolium*.

2 Drawing Sheets

BACKGROUND OF THE NEW PLANT

The present invention comprises a new distinct cultivar of Bidens, botanically known as *Bidens ferulifolium*, native to South USA and Mexico, and hereinafter referred to by the cultivar name 'Bidtis 1'.

The new Bidens was discovered by the inventor in a controlled environment in Enkhuizen, the Netherlands, as a naturally-occurring mutation of the *Bidens ferulifoium* 'Golden Eye' (unpatented). The new Bidens was observed as a single plant in a large population of plants of the parent cultivar.

The instant plant was grown under natural Dutch greenhouse spring conditions. The day/night temperature was 16/14° C. The light level was very much dependent on the weather. No extra light or growth regulators were applied. This new plant is an annual.

DESCRIPTION OF THE NEW CULTIVAR

The following detailed descriptions set forth the distinctive characteristics of this new Bidens plant. 'Bidtis 1' has been reproduced by terminal cuttings in Enkhuizen, the Netherlands, and all of the characteristics thereof have been determined to be firmly fixed. From December 2000 on, the variety is also intiated in tissue culture at SBW lab in Roelofarendsveen, the Netherlands, to maintain the variety. The plant history was taken on 5 months old plants, grown in a greenhouse in Enkhuizen.

Color references are primarily to the R.H.S. Color Chart of The Royal Horticultural Society of London.

DESCRIPTION OF THE DRAWINGS

This new Bidens plant is illustrated by the accompanying photogaphic drawings which shows blooms, buds and foliage of the plant in full color, the color shown being as true as can be reasonably obtained by conventional photographic procedures.

The plant was grown at day/night temperatures of 16/14° C. No growth regulators were applied. The plant was pinched one time to stimulate branching.

PLANT DESCRIPTION

Classification — Botanical: *Bidens ferulifolium.*
Parentage selection from: Bidens 'Golden Eye'.
Growth habit: Very compact, upright.
Plant height: 15–30 cm.
Spreading area of plant: 50–80 cm.
Growth rate: Compact.
Length of petiole: 1–2 cm.
Width/diameter of petiole: 1–2 mm.
Phyllaries: 4–5 mm.
Fruits: No fruits available.
Strength: Good tolerance for not-optimal conditions like heat, cold, dry conditions.
Branching character: Freely branching, very dense and bushy.
Branching: Number of branches per plant is very much depending on the number of pinchings. After 1 pinching there are approximately 5 to 10 branches on a 10 weeks-old-plant. After 17 weeks (and two times of pinching) the variety had 20 branches per plant.
Blooming period: Year round flowering depending on temperature, frost sensitive. 'Bidtis 1' can tolerate a little bit of frost for a short time (down to −2° C.). Maximum tolerated temperature is unknown, but it can stand the heat very well.
Rooting time: Initiation time: Summer: 14 days, Winter: 17 days. Development time: Summer: 17 days, Winter: 21 days. Soil temperature should be around 21° C., air temperature around 17° C.

COLORS

Older stems: Between 59A and 183B.
Stems: 152A.
Leaf veins: 137C.
Petioles: 199B.
Pollen: 23A.
Pistil: 17C.
Fruits: Sterile/no seed set.
Phyllaries: 147A.

STEM DESCRIPTION

Diameter: 1–2 mm.
Shape: Cylindrical.
Anthocyan pigmentation: Present in older stems.
Length of internode: Varying from 2.5–4 cm grown under Dutch spring conditions. Under low light conditions the internode length will be longer than under high light conditions.
Pubescence: Little white hairs (about 1 mm) About 100 hairs on 1 $cm^2$.

FOLIAGE DESCRIPTION

Phyllotaxis: Opposite, but alternate on flower stems.
Shape of leaf: 2-pinnate fern-like leaves.
Texture: Smooth young leaves.
Length: 10–35 mm.
Width: 5–20 mm.
Depth of incision: Fully incised.
*Color:*
*Upper side.*—137B.
*Lower side.*—137D.
Length of leaf stem: 5–15 mm.

FLOWER BUD DESCRIPTION

Pedicel length: 30–80 mm.
Size:
*Diameter.*—3–4 mm.
*Length.*—3–4 mm.
Shape: Oblong.

FLOWER DESCRIPTION

Lastiness of bloom: Approximately 3 weeks.
Number of flowers per plant: First flowers occur after 10 weeks growth. There are 20–30 flowers per plant after 17 weeks growth.
Direction: Ascending.
Shape of florets:
*Ray.*—Ovate with 2 light furrows.
*Disc.*—Tubular.
Disc floret size: 4–5 mm.
Disc floret number per flower head: ±50.
Diameter total flower head: 20–40 mm.
Borne: Solitary.
Form: Capitulum with 1 series of ray florets and more series of disc florets.
Flower color:
*Ray flower.*—Yellow 12A.
*Disc flower.*—Yellow orange 17A.
Overlapping of ray florets: Separate ray florets, but little overlap in flower head.
No. of ray florets: 5.
Receptacle shape: Brush-shape.
Receptacle height: 5 mm.
Involucre: Bracts in 2 series.
Size of the ray floret:
*Length.*—8–15 mm.
*Width.*—5–10 mm.
Fragrance: Weak.
Reproductive organs:
*Size.*—Pistil=±5 mm long, anther=±3 mm long.
*Shape.*—Stigma is decurrent.
*Number.*—±50–60 florets with pistils and anthers per flower head.
*Color.*—Pollen 23A, pistil 17C.
*Fertility.*—Sterile.

PHYSIOLOGICAL AND ECOLOGICAL CHARACTERISTICS

Good tolerance to heat. Strong resistance to pests and diseases. 'Bidtis 1' is more resistant to Botrytis and Powdery mildrew than *Bidens ferulifolium* in general.

We claim:

1. A new and distinct variety of Bidens plant, substantially as herein illustrated and described, characterized particularly as to novelty by its compact, upright plant habit with short internodes and bright golden yellow flowers.

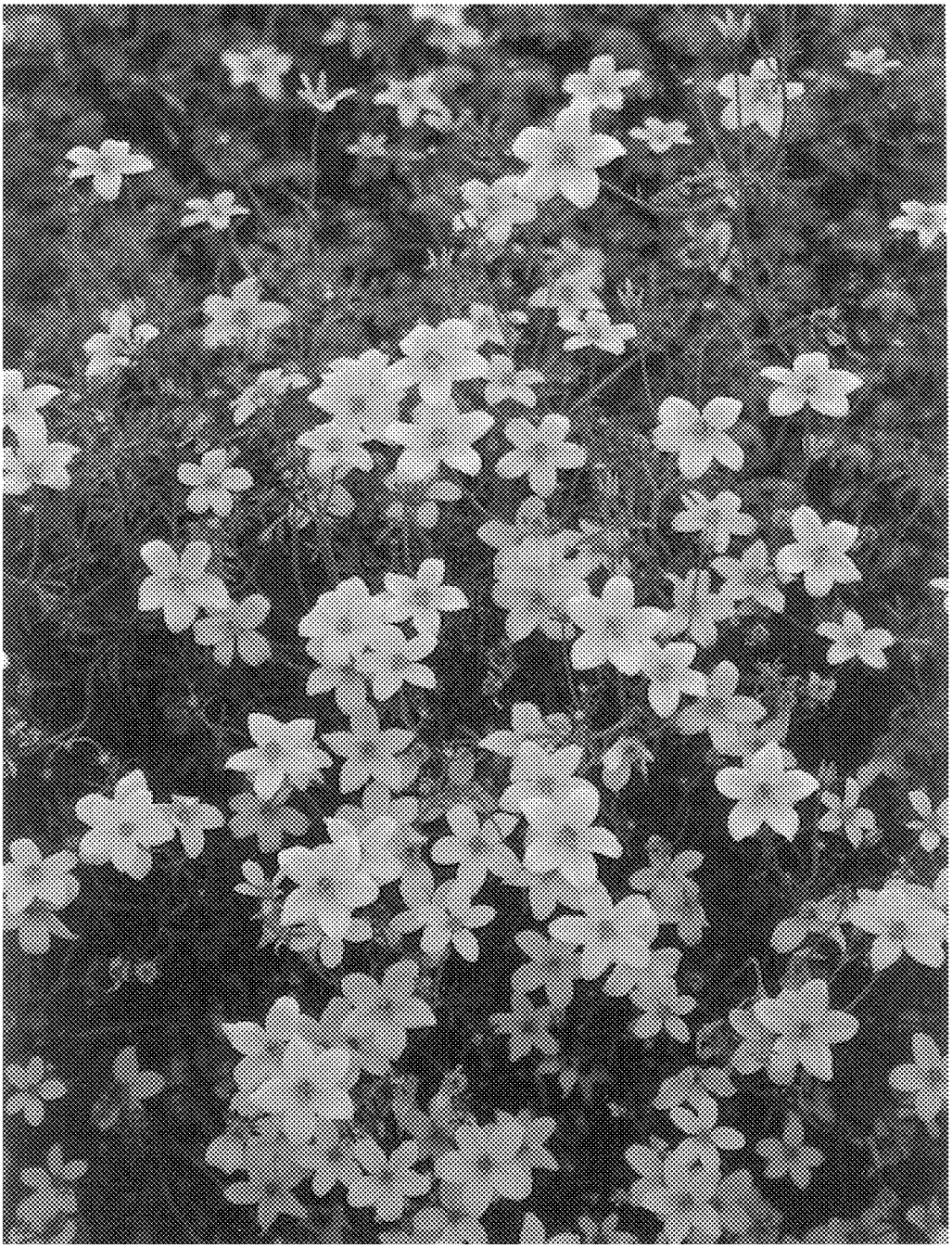

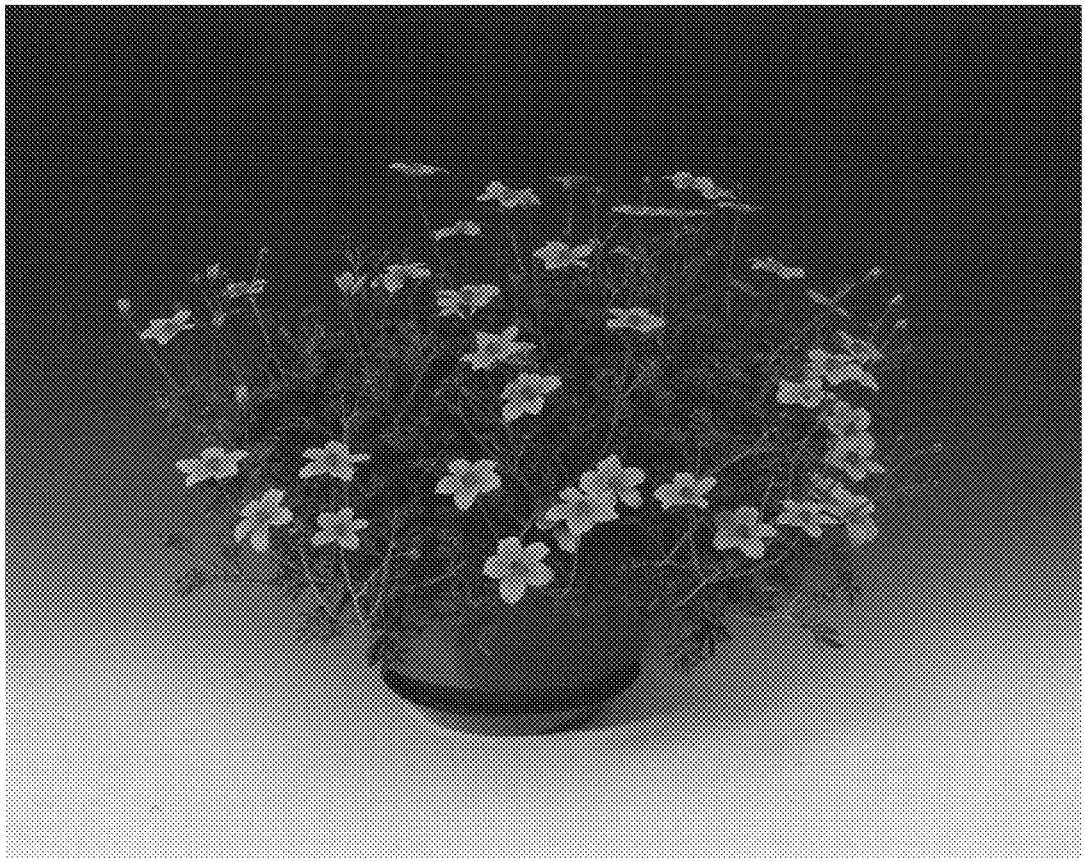

* * * * *